(12) United States Patent
Deckwer et al.

(10) Patent No.: US 6,995,005 B1
(45) Date of Patent: Feb. 7, 2006

(54) **ENZYME WHICH CLEAVES ESTER GROUPS AND WHICH IS DERIVED FROM *THERMONONOSPORA FUSCA***

(75) Inventors: Wolf-Dieter Deckwer, Braunschweig (DE); Rolf-Joachim Mueller, Braunschweig (DE); Ilona Kleeberg, Braunschweig (DE); Joop van den Heuvel, Braunschweig (DE)

(73) Assignee: Gesellschaft fuer Biotechnologische Forschung mbH (GBF), Braunschweig (DE)

( * ) Notice: Subject to any disclaimer, the term of this patent is extended or adjusted under 35 U.S.C. 154(b) by 133 days.

(21) Appl. No.: 10/089,392

(22) PCT Filed: Jul. 25, 2000

(86) PCT No.: PCT/EP00/07115

§ 371 (c)(1),
(2), (4) Date: Jul. 10, 2002

(87) PCT Pub. No.: WO01/23581

PCT Pub. Date: Apr. 5, 2001

(30) Foreign Application Priority Data

Sep. 30, 1999 (DE) ................................ 199 47 286

(51) Int. Cl.
*C12N 9/16* (2006.01)
*C12N 15/55* (2006.01)
*C12P 7/62* (2006.01)
*C07K 16/40* (2006.01)

(52) U.S. Cl. ...................... 435/196; 435/135; 435/346; 435/252.3; 530/387.9

(58) Field of Classification Search ................ 435/196, 435/346, 135, 253.3, 252.3; 530/387.9
See application file for complete search history.

(56) References Cited

U.S. PATENT DOCUMENTS 4,558,005 A * 12/1985 Goldwasser et al. ....... 435/7.92
6,254,645 B1 * 7/2001 Kellis et al. .................... 8/401

OTHER PUBLICATIONS

Hollick, G.E. (1982) Microbios. 35, 187-196.*
Kleeburg, I., et al. (1998) Appl. Environ. Microbiol. 64(5), 1731-1735.*
Fett, W.F., et al. (1993) J. Appl. Microbiol. 86, 561-568.*
Bachmann, S.L., et al. (1991) Appl. Environ. Microbiol. 57(8), 2121-2130.*
Drapeau, G.R., et al. (1972) J. Biol. Chem. 247(20), 6720-6726.*
Abdul-Razzaki, K.K., et al. (1989) Biochim. Biophys. Acta 996, 125-131.*
Kaoerzer et al., "Expression of synthetic genes encoding bovine and human basic fibroblast growth factors (bFGFs) in *Escherichia coli*", Gene 75 (1989) 21-30.
Perez et al., "Cloning, characterization, and expression in *Streptomyces lividans* 66 of an extracellular lipase-encoding gene from *Streptomyces* sp. M11", Gene 123 (1993) 109-114.

* cited by examiner

Primary Examiner—Charles L. Patterson, Jr.
(74) Attorney, Agent, or Firm—Frommer Lawrence & Haug LLP; Ronald R. Santucci

(57) ABSTRACT

The invention relates to an ester-group-cleaving enzyme obtainable by culturing the microorganism *Thermomonospora fusca* in a suitable nutrient medium, optionally in the presence of an inducer.

32 Claims, 4 Drawing Sheets

Fig. 3

```
Q59798      DNPYERGPA PTRASIEAPR GPYAVSQTSV SSLVVSGFGG        40
Q56008      ANPYERGPA PTNASIEASR GPYATSQTSV SSLVASGFGG        40
EGS-Enzym   .ANPYERGPN PTDALLEASS GPFSVSEENV SRLSASGFGG       39

Consensus   .ANPYERGPA PT.ASIEASR GPYAVSQTSV SSLVASGFGG        40

Q59798      GTIYYPTSTG DGTFGAVVVT PGFTATESSM AWLGPRLASQ        80
Q56008      GTIYYPTSTA DGTFGAVVIS PGFTAYQSSI AWLGPRLASQ        80
EGS-Enzym   GTIYYPRE-- NNTYGAVAIS PGYTGTEASI AWLGERIASH        77

Consensus   GTIYYPTST. DGTFGAVVIS PGFTATESSI AWLGPRLASQ        80

Q59798      GFVVFTIDTL TTLDQPDSRG RQMLAALDYL TER--SSART        118
Q56008      GFVVFTIDTN TTLDQPDSRG RQLLSALDYL TQR--SSVRT        118
EGS-Enzym   GFVVITIDTI TTLDQPDSRA EQLNAALNHM INRASSTVRS        117

Consensus   GFVVFTIDT. TTLDQPDSRG RQLLAALDYL T.R..SSVRT        120

Q59798      RIDGTRLGVI GHSMGGGGTL EAAKSRPSLK AAIPLTPWNL        158
Q56008      RVDATRLGVM GHSMGGGGSL EAAKSRTSLK AAIPLTGWNT        158
EGS-Enzym   RIDSSRLAVM GHSMGGGGTL RLASQRPDLK AAIPLTPWHL        157

Consensus   RID.TRLGVM GHSMGGGGTL E.AKSRPSLK AAIPLTPWNL        160

Q59798      DKTWPEVTTP TLVVGADGDT VAPVATHAKP FYSSLPSSTD        198
Q56008      DKTWPELRTP TLVVGADGDT VAPVATHSKP FYESLPGSLD        198
EGS-Enzym   NKNWSSVTVP TLIIGADLDT IAPVATHAKP FYNSLPSSIS        197

Consensus   DKTWPEVTTP TLVVGADGDT VAPVATHAKP FY.SLPSS.D        200

Q59798      RAYLELNNAT HFAPNLSNTT IAKYSVSWLK RFIDDDTRYE        238
Q56008      KAYLELRGAS HFTPNTSDTT IAKYSISWLK RFIDSDTRYE        238
EGS-Enzym   RAYLELDGAT HFAPNIPNKI IGKYSVAWLK RFVDNDTRYT        237

Consensus   RAYLEL.GAT HFAPN.SNTT IAKYSVSWLK RFID.DTRYE        240

Q59798      QFLCPLPVPD R--DIEEYRG TCPLGG                       262
Q56008      QFLCPIPRPS L--TIAEYRG TCPHTS                       262
EGS-Enzym   QFLCPGPRDG LFGEVEEYRS TCPF--                       261

Consensus   QFLCP.PRP. L...IEEYRG TCP...                       266
```

Q56008: triacylglycerol acyl hydrolase
Q59798: triacylglycerol lipase

ENZYME WHICH CLEAVES ESTER GROUPS AND WHICH IS DERIVED FROM *THERMONONOSPORA FUSCA*

The invention relates to an ester-group-cleaving enzyme (hereinafter also referred to as EGC enzyme) from *Thermomonospora fusca*, to a method for the preparation thereof and to its use in the degradation and treatment of ester-group-containing polymers and low molecular weight compounds.

INTRODUCTION AND STATE OF THE ART

Polymers and macromolecular materials that are susceptible to controlled biological degradation have become increasingly important in recent years. A number of such products are already commercially available on an industrial scale. Of those novel products, ester-group-containing polymers (e.g. polyesters, polyesterurethanes, polyesteramides) play a central role. Examples of biodegradable polyester-based plastics are, for example, poly(β-hydroxybutyrate-co-β-hydroxyvalerate), poly(ε-caprolactone) and poly(butylene succinate).

Since polymers cannot, owing to their molecular size, penetrate the outer membrane of microbial cells, the first step in degradation, which generally determines the rate, is a reduction in molecular weight (depolymerisation) by extracellular enzymes. Polyesters are accordingly potentially biodegradable, since the ester bonds constitute basic points of attack for such extracellular hydrolysing enzymes.

In the case of aliphatic polyesters, studies into biological degradation using such hydrolysing enzymes (e.g. lipases, PHB depolymerases) have been known for a long time [Tokiwa et al., Polym. Mater. Sci. Eng. 62 (1990), 988–992] [Jendrossek et al., Appl. Microbiol. Biotechnol. 46 (1996), 451–4631]. The material is incubated under suitable conditions with a corresponding enzyme and the degradation is determined by the formation of cleavage products in the surrounding medium or by the weight loss of the samples. In the case of natural polyhydroxyalkanoates, there were generally used hydrolases (PHB depolymerases) that had been specially isolated for the purpose, whereas for the degradation of synthetic polyesters there were used commercial lipases etc. that had not been specially isolated for the purpose of polymer degradation.

Whilst many aliphatic polyesters have proved in principle to be susceptible to biological attack, aromatic polyesters [e.g. poly(ethylene terephthalate), poly(propylene terephthalate), polybutylene terephthalate)] are known to be biologically resistant. In order to utilise the processing and application properties of the aromatic structures, which are better than those of aliphatic polyesters, in recent years biodegradable aliphatic-aromatic copolyesters have been developed and are manufactured on an industrial scale [Press information from BASF AG, Ludwigshafen, for the K'98 Trade Fair in Düsseldorf, of 17.03.98].

As a result of the introduction of aromatic components, however, the rate of biological degradation is significantly reduced [Müller et al., Polym. Degrad. Stab. 59 (1998), p. 203–208]. Thus, for example, Jun et al., [Jun et al., J. Environ., Polym. Degrad. 2(1) (1994), p. 9–18] come to the conclusion that copolyesters of PET and PCL are not significantly attacked by lipases (e.g. *Pseudomonas* sp. lipase).

Degradation of, in particular, polyesteramides using various customary commercial lipases has recently been described in terms of technical aspects [WO 98/36086]. That Patent Specification also describes the decomposition of a copolyester of butanediol, terephthalate (40 mol %) and adipate (60 mol %). The reactions, which are claimed to be suitable for technical applications, are achieved by, for example, 50 mg of enzyme (lipase from *Candida antarctica*) to 0.3–1.8 g of a polyesteramide in film or plate form. The rates of degradation obtained are in the region of 600 mg degradation/week. For the described degradation of the aliphatic-aromatic copolyester, an amount of enzyme of 1% (in 100 ml of buffer) must be added to a fine powder of the copolyester. Despite the considerably larger surface area covered as a result of the small particle size, a degradation of only 230 mg/week is obtained.

It has recently been shown that aliphatic-aromatic copolyesters can be degraded by microorganism strains from the group of Actinomycetes [Kleeberg et al., Appl. Environ. Polym. Degrad. 64(5), (1998), 1731–1735].

Nonetheless, there is still a need for a highly active ester-group-cleaving enzyme that is capable of degrading polyester-based polymers.

Surprisingly, it has been found, according to the invention, that biodegradable polyester-group-containing polymers, especially also aliphatic-aromatic copolyesters, can be depolymerised and broken down into low molecular weight fragments at an exceptionally high rate of degradation using the extracellular enzyme according to the invention, specified in more detail hereinafter, from the microorganism *Thermomonospora fusca*, which belongs to the Actinomycetes, especially the strain *Thermomonospora fusca* DSM 43793, on its own or in a mixture with other enzymes.

BRIEF DESCRIPTION OF THE DRAWINGS

FIG. 3: This figure shows the amino acid sequence of the ester group-cleaving enzyme (SEQ ID No: 1) and the alignment with triacylglycerol-lipase from *Streptomyces albus* G (SEQ ID No. 2) and with triacylglycerol-acyl hydrolase from *Streptomyces* sp. M11 (SEQ ID No. 3).

Figure 1:
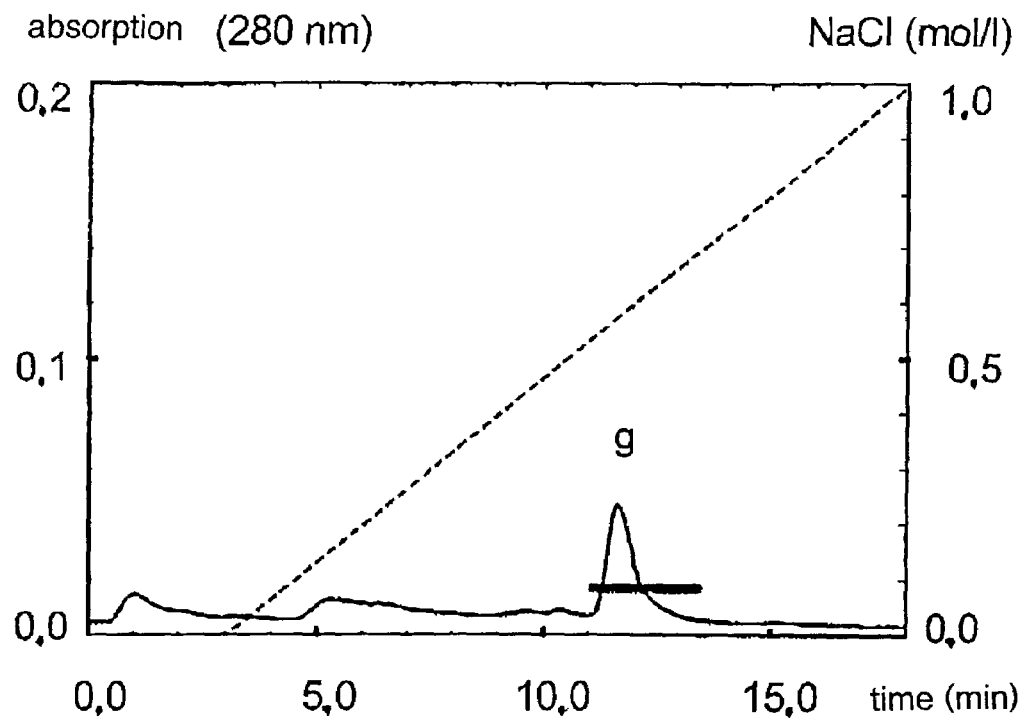
FIG. 1: This figure shows an elution profile of a concentrate of a supernatant of a culture of *Thermomonospora fusca* DSM 43793. The black band indicates fractions that exhibit ester group-cleaving activity.

The invention accordingly relates to an ester-group-cleaving enzyme according to patent claim 1, a synthetic peptide or protein according to patent claim 6, polyclonal and monoclonal antibodies according to patent claims 7 and 8, hybridoma cells according to patent claim 9, an ester-group-cleaving composition according to patent claim 11 and to the use of an ester-group-cleaving enzyme, synthetic peptide or protein or of an ester-group-cleaving composition according to patent claim 13.

Advantageous embodiments are given in the dependent claims.

More specifically, but without implying any limitation, the invention relates to an ester-group-cleaving enzyme obtainable by culturing the microorganism *Thermomonospora fusca* in a suitable nutrient medium, optionally in the presence of an inducer.

Preferably, the ester-group-cleaving enzyme according to the invention originates from the *Thermomonospora fusca* strain that has been deposited with the Deutschen Sammlung für Microorganismen [German Collection of Microorganisms] under the number DSM 43793.

The culture can be carried out by batch, fed batch or continuous operation in synthetic or complex media. The microorganisms can be free or immobilised on a solid carrier. In principle, both natural and genetically modified microorganisms are suitable.

Suitable inducers for the production of the enzyme are, for example, the substrates themselves, e.g. aliphatic polyesters and/or oligoesters, aliphatic-aromatic copolyesters.

In a preferred embodiment, the ester-group-cleaving enzyme according to the invention is also isolated from the nutrient medium by obtaining an enzyme-containing culture supernatant from the nutrient medium, for example by centrifugation, which supernatant may optionally be concentrated, for example by ultrafiltration and/or ammonium sulphate precipitation, whereupon the enzyme is purified by customary biochemical methods of purification, for example by chromatography, especially by ion exchange chromatography and/or hydrophobic interaction chromatography.

The ester-group-cleaving enzyme from *Thermomonospora fusca* DSM 43793 according to the invention is characterised by the following parameters:

molecular weight: 27400 d (determined by SDS gel electrophoresis) or 28200 d (calculated on the basis of the amino acid sequence);
temperature optimum/range: 65° C. (30–80° C.);
temperature stability: 70° C./30 min.;
pH optimum/range: 6–7 (4->8); isoelectric point: 6.4.

The substrate specificity encompasses ester-group-containing polymers, triglycerides and phthalic acid esters.

According to a preferred embodiment, the ester-group-cleaving enzyme from *Thermomonospora fusca* DSM 43793 according to the invention has the amino acid sequence of SEQ ID NO: 1, as shown below:

corresponding synthetic peptide or protein having identical function and/or amino acid sequence, and also to hybridoma cells that produce the monoclonal antibodies. The preparation of poly-or mono-clonal antibodies and the preparation of hybridomas that produce the latter have been known for a long time (see, for example: E. Harlow, D. Lane, "Antibodies, A Laboratory Manual", Cold Spring Harbor Laboratory, 1988; E. Lidell, I. Weeks, "Antikörper-Techniken", Spektrum Akademischer Verlag, 1996), and so require no further explanation.

The invention relates also to ester-group-cleaving compositions that comprise an ester-group-cleaving enzyme according to the invention and/or a corresponding synthetic peptide or protein having identical function and/or amino acid sequence and optionally additional enzymes, stabilisers, suitable surface-active substances and/or suitable organic solvents.

Preferably the additional enzymes are hydrolases, especially esterases, proteases, cutinases, lipases, phospholipases and lysophospholipases.

Especially preferably those hydrolases originate from microorganisms selected from *Pseudomonas* sp., *Rizomucor miehei, Candida cylindracea, Candida antartica, Aspergillus niger, Chromobacterium viscosum, Commamonas acidovorans, Rhizopus arrhizus* and *Rhizopus delamar*. Especially suitable are also the microroganisms disclosed in WO 98/36086 (Bayer AG), to which reference is expressly made herein.

The invention relates also to the use of an ester-group-cleaving enzyme according to the invention or of a synthetic peptide or protein having identical function and/or amino acid sequence or of an ester-group-cleaving composition according to the invention for the degradation of ester-group-containing low molecular weight and/or macromolecular synthetic or natural compounds.

Preferably the ester-group-containing macromolecular compounds are aliphatic, cycloaliphatic, aliphatic-aromatic, partially aromatic or aromatic polyesters or copolyesters, polyesteramides, polyestercarbonates or polyesterurethanes, the chain of which may be extended and which may be branched or crosslinked.

The ester-group-containing macromolecular compounds can be in any desired form and can form, for example, copolymers, mixtures and blends, composites, laminates or adhesive bonds with other materials.

| | | | |
|---|---|---|---|
| ANPYERGPNP | TDALLEASSG | PFSVSEENVS | RLSASGFGGG |
| TIYYPREN | NTYGAVAISP | GYTGTEASIA | WLGERIASHG |
| FVVITIDTIT | TLDQPDSRAE | QLNAALNHMI | NRASSTVRSR |
| IDSSRLAVMG | HSMGGGGTLR | LASQRPDLKA | AIPLTPWHLN |
| KNWSSVTVPT | LIIGADLDTI | APVATHAKPF | YNSLPSSISK |
| AYLELDGATH | FAPNIPNKII | GKYSVAWLKR | FVDNDTRYTQ |
| FLCPGPRDGL | FGEVEEYRST | CPF | | or a mutated amino acid sequence resulting from substitution, insertion or deletion of amino acids, which mutated amino acid sequence yields an isofunctional enzyme.

The above amino acid sequence or parts thereof can of course also be prepared synthetically by conventional methods, for example using an automatic peptide synthesizer.

The invention relates also to polyclonal and monoclonal antibodies that are directed specifically against an ester-cleaving enzyme according to the invention or against a In the method for the degradation of ester-group-containing low molecular weight and/or macromolecular (polymeric) compounds using the ester-group-cleaving enzyme according to the invention (or an enzyme prepared synthetically from the amino acid sequence) or a composition comprising such an enzyme, it is possible to achieve rates of decomposition that are markedly superior to those of systems known hitherto and that enable technical exploitation of the enzymatic treatment of ester-group-containing polymers. This is especially the case for aliphatic-aromatic copolyesters and polyester blends, which are economically very important.

The use of the ester-group-cleaving enzyme according to the invention (or of an enzyme prepared synthetically from the amino acid sequence) or of a composition comprising such enzymes in the treatment of the polymers mentioned above and hereinbelow in technically relevant forms, for example films, injection-moulded parts, coatings, laminates, foams, particles, adhesive bonds, can be used to increase the rate of metabolisation by microorganisms, to process products in the context of recycling (e.g. to dissolve adhesive bonds or remove coatings), to recover polymer building blocks from biodegradable polymers or to modify the surface of products made from polyesters.

The treatment of the polymers with a suitable enzyme formulation, for example in the form of a crude culture supernatant of *Thermomonospora fusca*, which may optionally be concentrated, a purified enzyme or a synthetic enzyme or a composition comprising such enzymes, can be effected, for example, in an aqueous solution or by application of the enzyme formulation to the polymeric materials.

Low molecular weight ester compounds play a part as additives in various polymers. Such compounds can also be cleaved by the enzyme according to the invention.

The ester-group-containing polymers that can be degraded by the enzyme according to the invention (or by an enzyme prepared synthetically from the amino acid sequence) and/or by the composition comprising such enzymes include, in addition to the polymers already mentioned above, for example, the following:

ester-group-containing synthetic and natural polymers, especially lignins, lignocellulose, cutin, suberin, aliphatic polyesters, especially those disclosed in WO 98/36086 (Bayer AG), to which reference is expressly made herein, especially polycaprolactone, aromatic or partially aromatic copolyesters, especially those disclosed in WO 98/36086 (Bayer AG), especially those containing terephthalic acid, more especially copolyesters of 1,4-butanediol, terephthalic acid and adipic acid (BTA), especially containing 30–70 mol % of terephthalic acid, polyesteramides, especially those disclosed in WO 98/36086 (Bayer AG), polymers containing urethane and ester groups, that is to say polyesterurethanes, and segmented polyurethanes.

The chain of the polyesters may be extended and the polyesters may be branched or crosslinked.

Especially preferred specific polyesters are poly(propylene succinate), poly(butylene succinate), poly(butylene succinate-co-ethylene succinate), a copolymer of succinic acid/adipic acid/1,2-ethanediol/1,4-butanediol, copolymers of 1,4-butanediol/adipic acid/terephthalic acid.

The ester-group-containing polymers that can be degraded by the enzyme according to the invention (or by an enzyme prepared synthetically from the amino acid sequence) and/or by the composition comprising such enzymes may be present, for example, in the form of:

copolymers or mixtures (blends) of two or more of the above-mentioned polymers;
composites or laminates of two or more of the above-mentioned polymers or copolymers or blends thereof;
composites, laminates or adhesive bonds with natural or modified natural polymeric materials, especially starch and/or cellulose (e.g. paper);
composites, laminates or adhesive bonds with other materials that are not necessarily biodegradable (e.g. glass);
polymer formulations comprising customary fillers, fibre reinforcers, auxiliaries, stabilisers.

The use according to the invention includes the treatment of polymers in the form of particles, suspensions, emulsions, coatings, adhesive bonds, films, mouldings, fibres or webs, wovens and foams. The materials can be used untreated or pretreated chemically, thermally or mechanically.

The enzyme is used, for example, in a buffered solution or in an unbuffered solution, optionally with adjustment of the pH value.

The application is effected, for example, by introducing ester-group-containing substances into suitable enzyme solutions or by applying a suitable enzyme formulation to corresponding substance surfaces.

Further possible uses of the enzyme according to the invention relate to the treatment of the above-defined materials for the purpose of pre-treatment in the course of disposal, the treatment of materials for the purpose of separating product components, the treatment of materials for the purpose of recovering individual material constituents or all the material constituents and the treatment of materials for the purpose of altering surface properties.

The following Examples serve to illustrate the invention and are not to be regarded as limiting.

1. Culture of *Thermomonospora fusca* DSM 43793.

A sterile culture flask without baffles, which can be sealed with an aluminium lid, is filled to two centimeters with sterile medium (corresponding to DIN V 54900, Part 2). 3 g/liter of a copolyester synthesised from 1,4-butanediol, terephthalic acid ester and adipic acid are added to the flask and inoculated with 1% by volume of the inoculum from a preculture of *Thermomonospora fusca*. The culture is incubated for 18 hours at 55° C. on a rotary shaker at 120 rev/min.

After stopping the culture, the solids are removed by centrifugation at 8000×g for 20 minutes at 10° C. The supernatant contains the ester-cleaving enzyme.

2. Degradation of an Aliphatic-Aromatic Copolyester with *Thermomonospora fusca* in the Culture Supernatant.

*Thermomonospora fusca* DSM 43793 is cultured in a mineral salt medium (see Example 1) for 24.8 hours at 55° C. 2 ml of the organism-free culture supernatant are introduced into a test tube. A circular polymer film (diameter 0.9 cm) of a copolyester of butanediol, terephthalic acid and adipic acid (40 mol % terephthalic acid in the acid component) is added to the culture supernatant and incubated for 24 hours at 55° C., after which the weight loss of the film is 2.575 mg/cm$^2$ surface area.

3. Isolation of the Ester-Cleaving Enzyme According to the Invention.

Concentration:

The culture supernatant of Example 1 is concentrated to 5% of the original volume in an Amicon ultrafiltration chamber (volume: 50 ml, filtration surface area: 47 mm$^2$) at a pressure of 3 bar and using a membrane having a cut-off of 10 Kd.

Further purification is effected using a standard FPLC system, "LCC-Plus", having automatic equilibration, injection and elution (Pharmacia, Uppsala, Sweden). The concentrated protein in the culture supernatant (2.1 mg) is purified in a first step over an ion exchange column.

Parameters:

Column: UNO-S1 column (column volume 1.3 ml, BioRad, Munich)

Starting buffer: 20 mM citrate buffer (pH 4.0)

Elution: (linear gradient) 1M NaCl in the starting buffer

Flow rate: 2 ml/min

FIG. 1 shows the elution profile, the black band indicating the fractions that exhibit ester-group-cleaving activity.

In a second step, fractions that are obtained by ion exchange chromatography and that exhibit activity are purified further by hydrophobic interaction chromatography (HIC).

116 $\mu$g of protein from fractions obtained by ion exchange chromatography are applied to a *Phenylsepharose* column.

Column: Phenylsepharose-CL4B column (column volume: 1.14 ml, Pharmacia. Uppsala, Sweden)

Starting buffer: 0.5M ammonium sulphate in 20 mM phosphate buffer (pH 7.1)

Elution: (stepped gradient) 30% isopropanol in 20 mM phosphate buffer (pH 7.1)

Flow rate: 0.3 ml/min.

Figure 2:
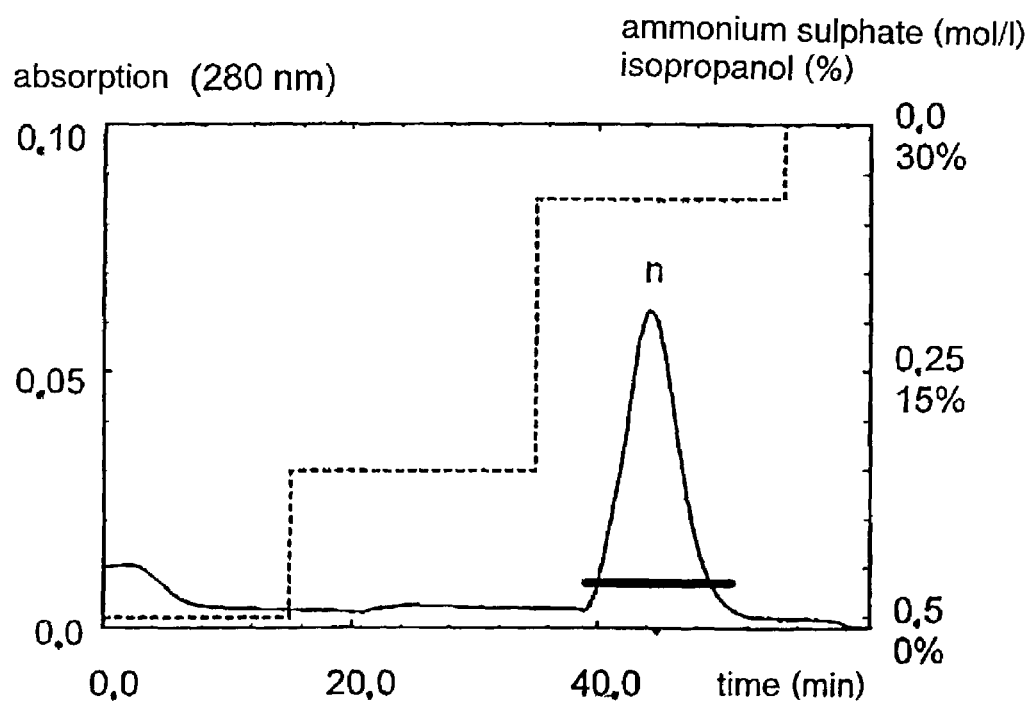
FIG. 2: This figure shows another elution profile of a concentrate of a supernatant of a culture of *Thermomonospora fusca* DSM 43793. The black band indicates fractions that exhibit ester group-cleaving activity.

FIG. 2 shows the elution profile, the black band indicating the fractions that exhibit ester-group-cleaving activity.

The culture supernatant has a specific activity of 3.3 U/mg. After ion exchange chromatography a specific activity of 218 U/mg is obtained and after HIC a specific activity of 360 U/mg is obtained.

Characterisation of the Enzyme According to the Invention.

FIG. 3 shows the amino acid sequence of the enzyme according to the invention and the alignment, for the purpose of sequence comparison, with triacylglycerol-lipase from *Streptomyces albus* G and with triacylglycerol-acylhydrolase from *Streptomyces* sp. M11. The multiple alignment was produced using the "PileUp" program (Wisconsin Package, Version 9.1, Genetics Computer Group, Madison, Wis., USA). The sequences of the two *Streptomyces* strains originate from the SP-TREMBL Databank (Release 7.0, 08/1998): Q56008 (*Streptomyces* sp. M11)(SEQ ID No: 3), Q59798 (*Streptomyces albus* G)(SEQ ID No: 2).

For the amino acid sequencing, the EGC enzyme was isolated from the foreign proteins still present after purification. This was carried out by separating out the proteins by means of preparative SDS gel electrophoresis and transfer to a PVDF membrane by Western blotting. After staining of the protein bands, the enzyme band was cut out from the membrane and sequenced.

In order to determine the entire sequence, the enzyme was digested with trypsin and GluC. GluC is an endoproteinase (*Staphylococcus aureus* Protease V8) which is a serine proteinase, and which selectively cleaves peptide bonds C-terminal to glutamic acid residues (see Drapeau, G. R. Boily, Y. and Houmard. J. (1972), Purification and properties of an extracellular protease of *Staphylococcus aureus*. J. Biol. Chem., 247, 6720–6726). The separation of the resulting peptides was effected by HPLC (reversed phase). The N-terminal sequence and the peptide fractions from the digestion of the BTA-hydrolase were analyzed by Edman degradation in an Applied Biosystems 473A Sequencer (gas-phase mode) or in a 494A Procise HT Sequencer (gas-phase and pulsed-liquid mode) using standard programs from the manufacturer.

The entire sequence of the enzyme was determined by sequence overlapping and comparison of the partial sequences of the EGC enzyme with the amino acid sequences of two known *Streptomyces lipases*.

4. Degradation of Ester-Group-Containing Polymers Using the Ester-Group-Cleaving Enzyme According to the Invention Under sterile conditions in test tubes, 1 ml of the purified enzyme solution (25 $\mu$g of enzyme in 20 mM phosphate buffer, pH 7.1) was added to a polymer film (d=0.9 cm). The test tubes were incubated for 17 hours at 55° C. The weight loss of the polymer films served as a measure of the enzyme activity.

Figure 4:
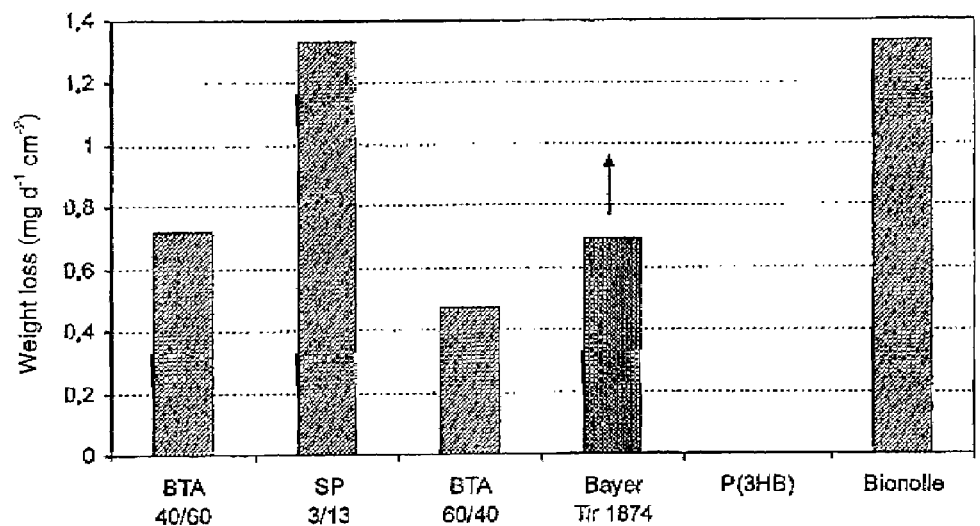
FIG. 4: This figure shows the weight loss by degradation of several ester-group containing polymers by means of the ester group-cleaving enzyme according to the invention.

In addition to the aliphatic-aromatic copolyesters BTA40:60 (40 mol % terephthalic acid in the acid component) and BTA60:40 (60 mol % terephthalic acid in the acid component), the following are subjected to degradation: an aliphatic polyester SP3:13 (synthesised from 1,3-propanediol and brassylic acid) and the commercial ester-group-containing polymers Bayer Tir 1874 (polyesteramide from Bayer AG), Bionolle (aliphatic polyester from Showa Highpolymers) and the natural bacterial polyester P(3HB). In respect of P(3HB), the ester-group-cleaving enzyme has no discernible activity. Bayer Tir 1874 was already fully solubilised at the time the sample was taken and the activity indicated represents a minimum value. The results are shown in FIG. 4.

5. Comparison of the Ester-Cleaving Enzyme According to the Invention with the Lipase of *Pseudomonas* sp.

Figure 5:
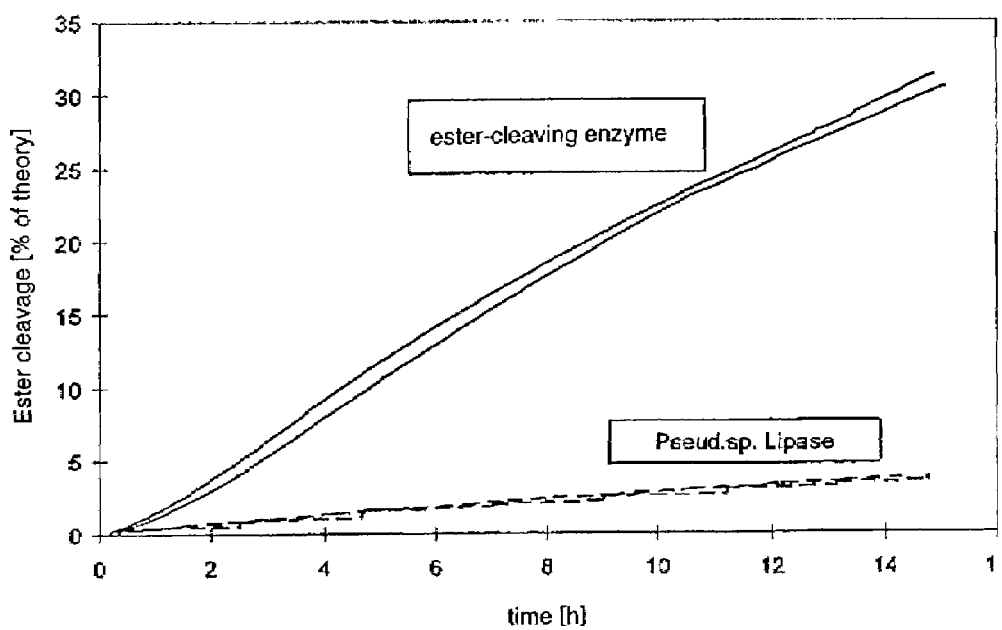
FIG. 5: This figure shows a comparison of the ester-cleavage of a polymer film by the ester cleaving-enzyme according to the invention and a lipase of *Pseudomonas* sp.

BTA40:60 films are each introduced into 6 ml of physiological sodium chloride solution (pH 7.0). 50 $\mu$g of the enzyme in question (ester-cleaving enzyme according to the invention or lipase of *Pseudomonas* sp. from SIGMA Chemical Co., EC 3.1.1.3) are added to the solution. The batch is incubated at the optimum temperature of the enzyme in question. The progress of degradation is monitored by titration of the free acids formed using 0.1M NaOH. The result is shown in FIG. 5.

In comparison with *Pseudomonas* sp. lipase, it is possible to obtain a substantially higher rate of hydrolysis using the enzyme according to the invention.

6. Cleavage of Triglycerides Using the Ester-Cleaving Enzyme According to the Invention and Using the Lipase of *Pseudomonas* sp.

5 ml of an emulsion solution (4.475 g of NaCl, 0.103 g of $KH_2PO_4$ dissolved in a mixture of 75 ml of distilled water and 135 ml of glycerol (99.5%), to which 1.5 g of gum arabic is added, the solution being made up to 250 ml with distilled water) and 4.5 ml of distilled water are added to 0.5 ml of each of the triglycerides.

The substrate solution is made up directly before the start of the enzyme test and is homogenised using an Ultraturrax for 1 minute at 13500 rev/min.

Figure 6:
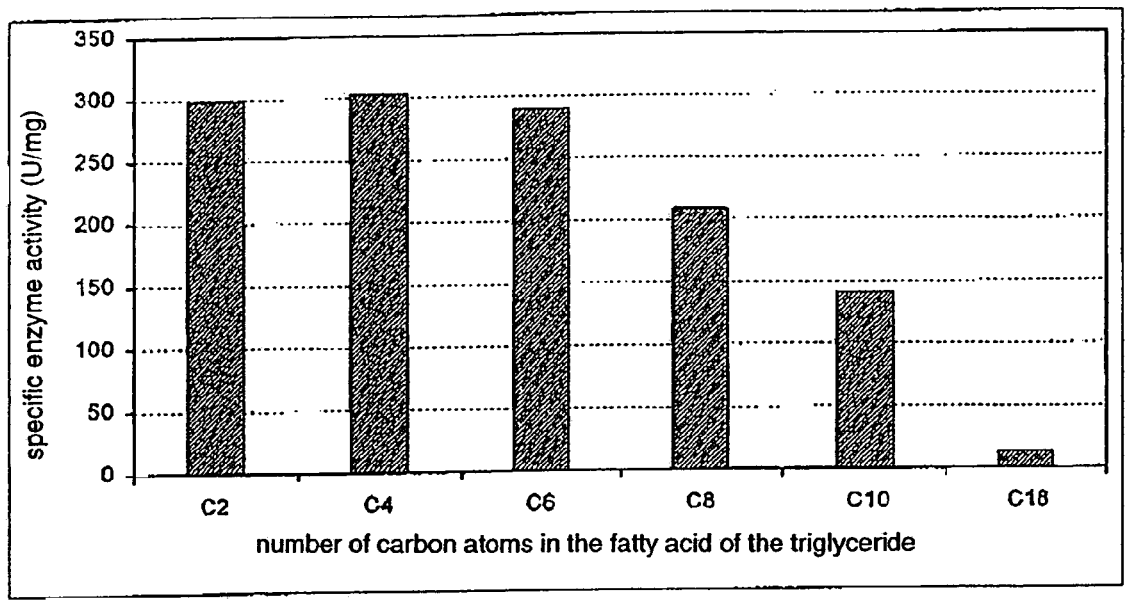
FIG. 6: This figure shows the specific activity of the enzyme according to the invention for different triglycerides.

The enzyme solution is then added to the substrate solution (20 $\mu$g of enzyme per 6 ml of substrate solution), the pH value is adjusted to pH 7.1 and the ester cleavage is monitored by titration using 0.1M NaOH. FIG. 6 shows the results for triglycerides having different numbers of carbon atoms in the fatty acid component.

A broad spectrum of fatty acids can be cleaved.

7. Cleavage of Phthalic Acid Esters Using the Ester-Cleaving Enzyme According to the Invention and Using the Lipase of *Pseudomonas* sp.

Figure 7:
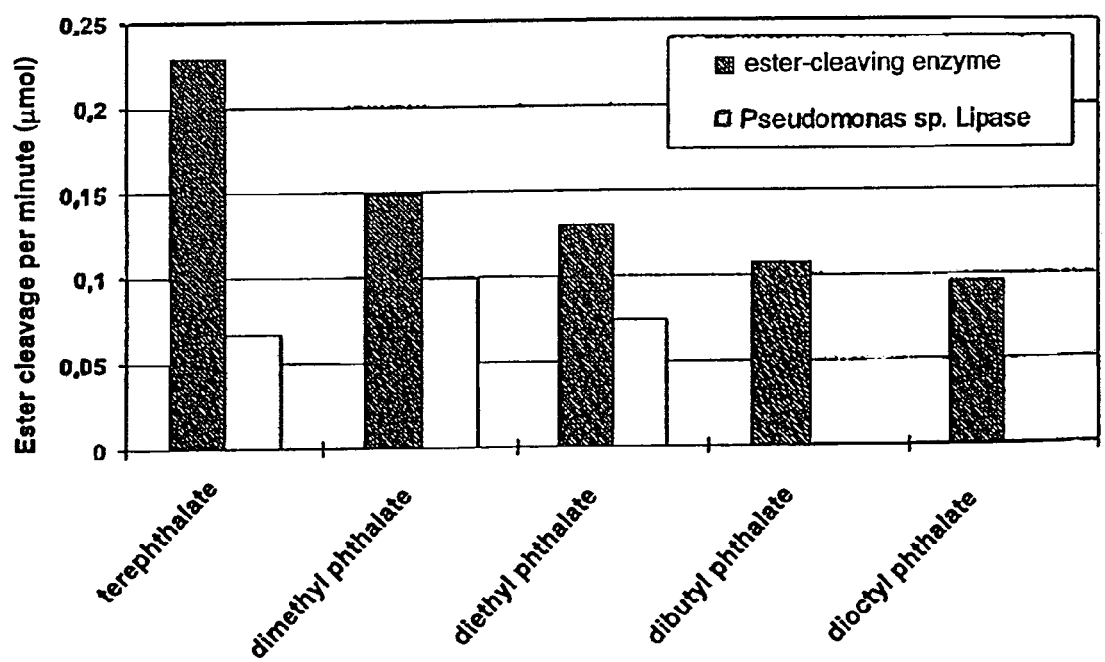
FIG. 7: This figure shows ester cleavages/min of different phthalic acid esters by means of the ester-cleaving enzyme according to the invention and the lipase of *Pseudomonas* sp.

The test batches correspond to those of Example 6. Phthalic acid esters having different alcohol components are used instead of the triglycerides. Whilst the lipase from *Pseudomonas* sp. is able to cleave only the dimethyl and diethyl esters, the enzyme according to the invention also hydrolyses esters having longer-chained alcohols. The rates of hydrolysis are higher than those of *Pseudomonas* sp. lipase. The results are shown in FIG. 7.

The invention claimed is:

1. An isolated ester-group-cleaving enzyme obtained by culturing the microorganism *Thermomonospora fusca* in a suitable nutrient medium, in the presence of an inducer, wherein the ezyme
   (i) cleaves ester groups of macromolecular compounds,
   (ii) is water soluble, and
   (iii) has a molecular weight of 27,400 Daltons to 28,200 Daltons.

2. The isolated ester-group-cleaving enzyme according to claim 1, wherein the microorganism is a *Thermomonospora fusca* strain that has been deposited with the Deutschen Sammlung für Mikroorganismen (German Collection of Microorganisms) under the number DSM 43793.

3. The isolated ester-group-cleaving enzyme according to claim 1, wherein the enzyme is isolated from the nutrient medium by obtaining an enzyme-containing culture supernatant from the nutrient medium, and
   purifying the enzyme by chromatography.

4. The isolated ester-group-cleaving enzyme according to claim 1, wherein the enzyme has a-molecular weight of 27400 d to 28200 d,
   an optimum temperature of 65° C., a functional temperature range of 30–80° C., temperature stability of 70° C./30 min, an optimum pH of 6–7 a functional pH range of 4->8, and an isoelectric point of 6.4.

5. The isolated ester-group-cleaving enzyme according to claim 1, wherein the enzyme has the amino acid sequence of SEQ ID NO: 1.

6. A synthetic peptide or protein comprising the amino acid sequence of the ester-group-cleaving enzyme according to claim 5.

7. A polyclonal antibody directed specifically against an ester-group-cleaving enzyme according to claim 1.

8. A monoclonal antibody directed specifically against an ester-group-cleaving enzyme according to claim 1.

9. A hybridoma cell that produces a monoclonal antibody according to claim 8.

10. An ester-group-cleaving composition that comprises an ester-group-cleaving enzyme according to claim 1 and at least one additional component comprised of additional enzymes, stabilisers, surface-active substances organic solvents.

11. The ester-group-cleaving composition according to claim 10, wherein the additional enzymes are selected from the group consisting of hydrolases, esterases, proteases, cutinases, lipases, phospho-lipases and lysophospholipases.

12. The ester-group-cleaving composition according to claim 11, wherein the hydrolases are from microorganisms selected from the group consisting of *Pseudomonas* sp., *Rizomucor miehei, Candida cylindracea, Candida antartica, Aspergillus niger, Chromobacterium viscosum, Commamonas acidovorans, Rhizopus arrhizus* and *Rhizopus delama*.

13. A method for the degradation of an ester-group-containing macromolecular compound, comprising the steps of:
   a) providing an ester-group-containing macromolecular compound;
   b) providing an ester-group-cleaving enzyme according to claim 1; and
   c) incubating said ester-group-containing macromolecular compound and said ester-group-cleaving enzyme for a suitable time and at a suitable temperature,
   such that the ester-group-containing macromolecular compound is degraded.

14. The method according to claim 13, wherein the ester-group-containing macromolecular compounds are aliphatic, cycloaliphatic, aliphatic-aromatic, partially aromatic, aromatic polyesters, aromatic copolyesters, polyesteramides, polyestercarbonates or polyester-urethanes.

15. The method according to claim 14, wherein the ester-group-containing macromolecular compounds form copolymers, mixtures and blends, composites, laminates or adhesive bonds with other materials.

16. A genetically modified microorganism producing, in culture, a protein having the amino acid sequence of SEQ ID NO 1.

17. A genetically modified microorganism according to claim 16 wherein the microorganism is a *Thermomonospora fusca* strain.

18. The isolated ester-group cleaving enzyme according to claim 3, wherein the culture supernatant is concentrated prior to purifying the enzyme by chromatography.

19. The isolated ester group cleaving enzyme according to claim 3, wherein said chromatography method comprises ion exchange chromatography or hydrophobic interaction chromatography.

20. A polyclonal antibody directed specifically against an ester-group-cleaving enzyme according to claim 5.

21. A polyclonal antibody directed specifically against a synthetic peptide or protein according to claim 6.

22. A monoclonal antibody directed specifically against an ester-group-cleaving enzyme according to claim 5.

23. A monoclonal antibody directed specifically against a synthetic peptide or protein according to claim 6.

24. A hybridoma cell that produces a monoclonal antibody according to claim 22.

25. A hybridoma cell that produces a monoclonal antibody according to claim 23.

26. An ester-group-cleaving composition that comprises an ester-group-cleaving enzyme according to claim 5 and at least one additional component comprised of additional enzymes, stabilisers, surface-active substances or organic solvents.

27. An ester-group-cleaving composition that comprises a synthetic peptide or protein according to claim 6 and at least one additional component comprised of additional enzymes, stabilisers, surface-active substances or organic solvents.

28. The ester-group-cleaving composition according to claim 26, wherein the additional enzymes are selected from the group consisting of hydrolases, esterases, proteases, cutinases, lipases, phospho-lipases and lysophospholipases.

29. The ester-group-cleaving composition according to claim 27, wherein the additional enzymes are selected from the group consisting of hydrolases, esterases, proteases, cutinases, lipases, phospho-lipases and lysophospholipases.

30. A method for the degradation of an ester-group-containing macromolecular compound, comprising the steps of:
   a) providing an ester-group-containing macromolecular compound;
   b) providing a synthetic peptide or protein according to claim 6; and
   c) incubating said ester-group-containing macromolecular compound and said synthetic peptide or protein for a suitable time and at a suitable temperature, such that the ester-group-containing macromolecular compound is degraded.

31. The method according to claim 30, wherein the ester-group-containing macromolecular compounds are aliphatic, cycloaliphatic, aliphatic-aromatic, partially aromatic, aromatic polyesters, aromatic copolyesters, polyesteramides, polyestercarbonates or polyester-urethanes.

32. The method according to claim 31, wherein the ester-group-containing macromolecular compounds form copolymers, mixtures an blends, composites, laminates or adhesive bonds with other materials.

* * * * *

SEQUENCE LISTING

<160> NUMBER OF SEQ ID NOS: 3

<210> SEQ ID NO 1
<211> LENGTH: 261
<212> TYPE: PRT
<213> ORGANISM: Thermomonospora fusca

<400> SEQUENCE: 1

```
Ala Asn Pro Tyr Glu Arg Gly Pro Asn Pro Thr Asp Ala Leu Leu Glu
 1               5                  10                  15

Ala Ser Ser Gly Pro Phe Ser Val Ser Glu Glu Asn Val Ser Arg Leu
            20                  25                  30

Ser Ala Ser Gly Phe Gly Gly Gly Thr Ile Tyr Tyr Pro Arg Glu Asn
        35                  40                  45

Asn Thr Tyr Gly Ala Val Ala Ile Ser Pro Gly Tyr Thr Gly Thr Glu
    50                  55                  60

Ala Ser Ile Ala Trp Leu Gly Glu Arg Ile Ala Ser His Gly Phe Val
65                  70                  75                  80

Val Ile Thr Ile Asp Thr Ile Thr Thr Leu Asp Gln Pro Asp Ser Arg
                85                  90                  95

Ala Glu Gln Leu Asn Ala Ala Leu Asn His Met Ile Asn Arg Ala Ser
            100                 105                 110

Ser Thr Val Arg Ser Arg Ile Asp Ser Ser Arg Leu Ala Val Met Gly
        115                 120                 125

His Ser Met Gly Gly Gly Gly Thr Leu Arg Leu Ala Ser Gln Arg Pro
    130                 135                 140

Asp Leu Lys Ala Ala Ile Pro Leu Thr Pro Trp His Leu Asn Lys Asn
145                 150                 155                 160

Trp Ser Ser Val Thr Val Pro Thr Leu Ile Ile Gly Ala Asp Leu Asp
                165                 170                 175

Thr Ile Ala Pro Val Ala Thr His Ala Lys Pro Phe Tyr Asn Ser Leu
            180                 185                 190

Pro Ser Ser Ile Ser Lys Ala Tyr Leu Glu Leu Asp Gly Ala Thr His
        195                 200                 205

Phe Ala Pro Asn Ile Pro Asn Lys Ile Ile Gly Lys Tyr Ser Val Ala
    210                 215                 220

Trp Leu Lys Arg Phe Val Asp Asn Asp Thr Arg Tyr Thr Gln Phe Leu
225                 230                 235                 240

Cys Pro Gly Pro Arg Asp Gly Leu Phe Gly Glu Val Glu Glu Tyr Arg
                245                 250                 255

Ser Thr Cys Pro Phe
            260
```

<210> SEQ ID NO 2
<211> LENGTH: 261
<212> TYPE: PRT
<213> ORGANISM: Streptomyces albus

<400> SEQUENCE: 2

```
Asp Asn Pro Tyr Glu Arg Gly Pro Ala Pro Thr Arg Ala Ser Ile Glu
 1               5                  10                  15

Ala Pro Arg Gly Pro Tyr Ala Val Ser Gln Thr Ser Val Ser Ser Leu
            20                  25                  30

Val Val Ser Gly Phe Gly Gly Gly Thr Ile Tyr Tyr Pro Thr Ser Thr
        35                  40                  45
```

-continued

```
Gly Asp Gly Thr Phe Gly Ala Val Val Thr Pro Gly Phe Thr Ala
        50                  55                  60

Thr Glu Ser Ser Met Ala Trp Leu Gly Pro Arg Leu Ala Ser Gln Gly
 65                  70                  75                  80

Phe Val Val Phe Thr Ile Asp Thr Leu Thr Leu Asp Gln Pro Asp
                85                  90                  95

Ser Arg Gly Arg Gln Met Leu Ala Ala Leu Asp Tyr Leu Thr Glu Arg
                100                 105                 110

Ser Ser Ala Arg Thr Arg Ile Asp Gly Thr Arg Leu Gly Val Ile Gly
            115                 120                 125

His Ser Met Gly Gly Gly Thr Leu Glu Ala Ala Lys Ser Arg Pro
        130                 135                 140

Ser Leu Lys Ala Ala Ile Pro Leu Thr Pro Trp Asn Leu Asp Lys Thr
145                 150                 155                 160

Trp Pro Glu Val Thr Thr Pro Thr Leu Val Val Gly Ala Asp Gly Asp
                165                 170                 175

Thr Val Ala Pro Val Ala Thr His Ala Lys Pro Phe Tyr Ser Ser Leu
                180                 185                 190

Pro Ser Ser Thr Asp Arg Ala Tyr Leu Glu Leu Asn Asn Ala Thr His
            195                 200                 205

Phe Ala Pro Asn Leu Ser Asn Thr Thr Ile Ala Lys Tyr Ser Val Ser
        210                 215                 220

Trp Leu Lys Arg Phe Ile Asp Asp Thr Arg Tyr Glu Gln Phe Leu
225                 230                 235                 240

Cys Pro Leu Pro Val Pro Asp Arg Asp Ile Glu Glu Tyr Arg Gly Thr
                245                 250                 255

Cys Pro Leu Gly Gly
            260

<210> SEQ ID NO 3
<211> LENGTH: 261
<212> TYPE: PRT
<213> ORGANISM: Streptomyces sp. M11

<400> SEQUENCE: 3

Ala Asn Pro Tyr Glu Arg Gly Pro Ala Pro Thr Asn Ala Ser Ile Glu
 1               5                  10                  15

Ala Ser Arg Gly Pro Tyr Ala Thr Ser Gln Thr Ser Val Ser Ser Leu
                20                  25                  30

Val Ala Ser Gly Phe Gly Gly Gly Thr Ile Tyr Tyr Pro Thr Ser Thr
            35                  40                  45

Ala Asp Gly Thr Phe Gly Ala Val Val Ile Ser Pro Gly Phe Thr Ala
        50                  55                  60

Tyr Gln Ser Ser Ile Ala Trp Leu Gly Pro Arg Leu Ala Ser Gln Gly
 65                  70                  75                  80

Phe Val Val Phe Thr Ile Asp Thr Asn Thr Thr Leu Asp Gln Pro Asp
                85                  90                  95

Ser Arg Gly Arg Gln Leu Leu Ser Ala Leu Asp Tyr Leu Thr Gln Arg
                100                 105                 110

Ser Ser Val Arg Thr Arg Val Asp Ala Thr Arg Leu Gly Val Met Gly
            115                 120                 125

His Ser Met Gly Gly Gly Ser Leu Glu Ala Ala Lys Ser Arg Thr
        130                 135                 140
```

-continued

```
Ser Leu Lys Ala Ala Ile Pro Leu Thr Gly Trp Asn Thr Asp Lys Thr
145                 150                 155                 160

Trp Pro Glu Leu Arg Thr Pro Thr Leu Val Val Gly Ala Asp Gly Asp
                165                 170                 175

Thr Val Ala Pro Val Ala Thr His Ser Lys Pro Phe Tyr Glu Ser Leu
            180                 185                 190

Pro Gly Ser Leu Asp Lys Ala Tyr Leu Glu Leu Arg Gly Ala Ser His
        195                 200                 205

Phe Thr Pro Asn Thr Ser Asp Thr Thr Ile Ala Lys Tyr Ser Ile Ser
    210                 215                 220

Trp Leu Lys Arg Phe Ile Asp Ser Asp Thr Arg Tyr Glu Gln Phe Leu
225                 230                 235                 240

Cys Pro Ile Pro Arg Pro Ser Leu Thr Ile Ala Glu Tyr Arg Gly Thr
                245                 250                 255

Cys Pro His Thr Ser
                260
```